(12) United States Patent
Niver

(10) Patent No.: US 10,617,405 B2
(45) Date of Patent: Apr. 14, 2020

(54) SUTURE CONSTRUCTS FOR LIGAMENT REPAIR AND METHODS OF USE THEREOF

(71) Applicant: Howmedica Osteonics Corp., Mahwah, NJ (US)

(72) Inventor: Ryan J. Niver, Glenview, IL (US)

(73) Assignee: Howmedia Osteonics Corp., Mahwah, NJ (US)

(*) Notice: Subject to any disclaimer, the term of this patent is extended or adjusted under 35 U.S.C. 154(b) by 598 days.

(21) Appl. No.: 15/417,557

(22) Filed: Jan. 27, 2017

(65) Prior Publication Data

US 2017/0303910 A1    Oct. 26, 2017

Related U.S. Application Data

(60) Provisional application No. 62/326,297, filed on Apr. 22, 2016.

(51) Int. Cl.
*A61B 17/56*   (2006.01)
*A61B 17/04*   (2006.01)
*A61B 17/06*   (2006.01)

(52) U.S. Cl.
CPC .... *A61B 17/0401* (2013.01); *A61B 17/06166* (2013.01); *A61B 2017/0496* (2013.01); *A61B 2017/564* (2013.01); *A61B 2017/567* (2013.01)

(58) Field of Classification Search
CPC . A61B 17/0401; A61B 17/56; A61B 17/7019; A61B 17/7022; A61B 17/7049; A61B 17/7052; A61B 17/7053; A61B 2017/567; A61B 5/4566; A61B 5/4571; A61B 5/4576; A61B 5/458; A61B 5/4585; A61B 5/459; A61B 5/4595
See application file for complete search history.

(56) References Cited

U.S. PATENT DOCUMENTS

| 5,372,146 | A  | 12/1994 | Branch |
| 6,635,073 | B2 | 10/2003 | Bonutti |
| 6,818,010 | B2 | 11/2004 | Eichhorn et al. |
| 6,972,027 | B2 | 12/2005 | Fallin et al. |

(Continued)

OTHER PUBLICATIONS

Cloutier et al., Total Knee Arthroplasty with Retention of Both Cruciate Ligaments. A Nine to Eleven-Year Follow-up Study, Journal of Bone and Joint Surgery Am, vol. 81 (5): pp. 697-702, May 1999.

*Primary Examiner* — Sarah W Aleman
(74) *Attorney, Agent, or Firm* — Lerner, David, Littenberg, Krumholz & Mentlik, LLP

(57) ABSTRACT

Embodiments of the invention describe methods of implanting and setting an adjustable suture structure capable of maximizing and controlling the available range of motion in a defective joint. The adjustable suture structure can augment a joint repair following surgery or be used as a standalone construct. One embodiment involves completion of a standard ligament repair, followed by the implant of anchors to secure sutures between bone locations proximal to the native origin of the repaired ligaments. Each of the sutures is implanted with at least some slack. Once the sutures are secured, the first suture is alternatively tensioned and moved through a range of motion, followed by the same process in a second suture. The steps are performed iteratively until the range of motion is controlled or limited sufficiently to protect the repaired ligaments.

20 Claims, 6 Drawing Sheets

(56) References Cited

U.S. PATENT DOCUMENTS

| | | |
|---|---|---|
| 7,585,311 B2 | 9/2009 | Green et al. |
| 7,905,904 B2 | 3/2011 | Stone et al. |
| 8,361,113 B2 | 1/2013 | Stone et al. |
| 8,696,704 B2 | 4/2014 | Selvitelli et al. |
| 8,961,576 B2 * | 2/2015 | Hodge ............... A61B 17/0401 606/232 |
| 2004/0138683 A1 | 7/2004 | Shelton et al. |
| 2008/0312689 A1 | 12/2008 | Denham et al. |
| 2010/0063542 A1 | 3/2010 | van der Burg et al. |
| 2013/0131722 A1 | 5/2013 | Marchand et al. |
| 2014/0067063 A1 * | 3/2014 | Bonutti ................... A61F 2/441 623/13.15 |

* cited by examiner

SUTURE CONSTRUCTS FOR LIGAMENT REPAIR AND METHODS OF USE THEREOF

CROSS-REFERENCE TO RELATED APPLICATION

This application claims the benefit of the filing date of U.S. Provisional Patent Application No. 62/326,297, filed Apr. 22, 2016, the disclosure of which is hereby incorporated by reference herein.

BACKGROUND OF THE INVENTION

In surgical practice, there is an ongoing need for improved methods to accelerate recovery time following standard ligament repairs such as the re-attachment or repair of tendons, ligaments, or other tissue which has separated from the bone. The separation, tear or other deficiency can be due to ligament injury, trauma, chronic laxity, genetic defects, and various surgical procedures, among other causes. Typical procedures for the repair of ligaments include the use of bone tunnels and suture anchors.

When standard repair methods are used, there is often a need for the patient to be immobilized or risk a post-surgical failure or poor healing. The source of this risk is in no small part due to an observed weakness and/or loss in flexibility in the ligaments during a recovery period following surgery where the joint and related soft tissue is not being used. This weakness and poor flexibility can prevent the safe exertion of stress on the repaired ligaments. Thus, post-surgical instructions typically include steps to prevent any motion in the repaired joint post-operatively. This is intended to minimize the possibility of rupture or other forms of damage due to stress on the repaired ligament.

Occasionally, following surgery or following a period of time where the joint is prohibited from movement, external bracing systems have been used which allow for limited motion of the joint for a period of time. However, such external braces are cumbersome and difficult to use in everyday life. Similarly, sutures have been used to replace native soft tissues (i.e., ligaments and tendons) or elastic bands have been used to supplement repaired soft tissues to promote joint stability. However, they do not provide for a limit on the mobility of the joint. As such, these suture bracing systems allow for the possibility of over-exertion of the joint which could result in the aforementioned risk of injury to the repair.

Thus, a need exists for an internal bracing system that can be a standalone construct or provide augmentation to soft tissue repair to stabilize the joint and limit mobility of the joint following surgery. Similarly, a need also exists for a method that provides for implantation of such an internal bracing system that allows for a controlled and limited range of motion where a suture structure is implanted as a standalone construct or as an augmentation to repaired soft tissue.

BRIEF SUMMARY OF THE INVENTION

Described herein are methods of implanting and tensioning an internal stabilization system, such as an adjustable suture structure, to provide stability in a defective joint. In one embodiment, a method of joint stabilization is used to assemble a suture configuration to stabilize a joint. The method involves implanting a first anchor into a first location in a bone; loading a suture having first and second ends into the first anchor; loading at least one of the first and second ends of the suture into a second anchor; implanting the second anchor into a second location in a bone such that there is slack in a portion of the suture between the first anchor and the second anchor; and alternatively or simultaneously, tensioning the suture and moving the joint through a range of motion until the tensioning increases tension in the suture to a final tension at which the range of motion of the joint is limited to prevent over-exertion of the joint in at least one direction of motion.

In a variant of the above method, prior to implanting the first and second anchors, the first and second bone locations are established based on native origins of one or more ligaments. In one alternative of this variant, implanting the first and second anchors involves placing each anchor under a repaired ligament. This alternative provides an adjustable suture structure where the sutures augment and protect the repaired ligament to stabilize the joint when the tension in the sutures is the final tension. In another alternative of this variant, the joint is exerted in the at least one direction of motion such that the exertion is up to and including an amount that causes tension in the suture to reach the final tension. The final tension in the suture prevents over-exertion of the joint in the at least one direction of motion by preventing any additional movement of the joint in the at least one direction of motion.

In another variant of the above method, the loading step further comprises loading a third and fourth end of the second suture into the first anchor so that a total of four suture ends extend from the first anchor. The four suture ends stem from the combined first and second sutures. In one alternative of this variant, implanting the first and/or second anchor into the bone is completed prior to loading the first suture into the first and/or second anchor. In another alternative, the method also includes loading at least one of the other of the first, second, third and fourth ends of the sutures into a third anchor after implanting the first anchor. The third anchor is then implanted into a third location in a bone. In its secured position, the first or second suture is secured between the first anchor and third anchor so that it includes slack. These steps are performed prior to tensioning the first or second suture. In this alternative, tensioning of the first suture ceases at an intermediate tension prior to reaching the final tension. Following tensioning of the suture secured to the second anchor, the first and/or second suture is tensioned, either alternatively or simultaneously, in conjunction with moving the joint through the range of motion. In yet another alternative of this variant, after tensioning the first and/or second suture, the sequence of tensioning the suture or sutures between the first and second anchors followed by the suture or sutures between the first and third anchors is repeated one or more times until the tension between both the first and second anchors and first and third anchors corresponding to the limited range of motion is obtained. In other alternatives of this variant, implanting the first, second and third anchors involves placing each anchor under one or more repaired ligaments and then into bone at the first, second and third bone locations, respectively. In this arrangement, the final tension in the sutures augments and protects the repaired ligament or ligaments to stabilize the joint.

In another embodiment, a method of joint stabilization uses one or more sutures to stabilize a joint. The method involves tensioning a first suture connected to a first bone at a first location and a second bone at a second location. The first location corresponds to a first native origin of a first ligament and the second location corresponds to a second native origin of the first ligament. During tensioning, an additional step of moving the joint through a range of motion is performed either alternatively or simultaneously. These steps determine an available range of motion of the first bone relative to the second bone with incremental levels of tension. Tensioning of the first suture and moving of the joint through a range of motion ceases prior to reaching a first tension. The first tension is an amount sufficient to prevent over-exertion of the joint in at least one direction of motion. This is followed by tensioning the second suture connected to the first bone at a first location and a third bone at a second location. The first location corresponds to the first native origin of a second ligament and the second location corresponds to a second native origin of the second ligament. During tensioning, an additional step of moving the joint through a range of motion is performed either alternatively or simultaneously. These steps determine an available range of motion of the first bone relative to the third bone with incremental levels of tension. Tensioning of the second suture and moving of the joint through a range of motion ceases prior to teaching a second tension. The second tension is an amount sufficient to prevent over-exertion of the joint in at least one direction of motion. The tensioning and moving steps for the first and second sutures are then repeated one or more times until the tension in the first and second sutures limits the range of motion in the joint in at least one direction of motion.

In a variant of the above method, the connections to the first, second and third bones are made by implanting a first anchor into the first bone, a second anchor into the second bone and a third anchor into the third bone. In one alternative of this variant, tensioning of the first suture involves interconnecting a tool with the second anchor and manipulating the tool to cause rotation of the second anchor. Similarly, tensioning of the second suture involves interconnecting the tool with the third anchor and manipulating the tool to cause rotation of the third anchor. In yet another alternative of this variant, the tool interconnected with the second anchor is different from the tool interconnected with the third anchor. In this instance, manipulating the tools involves rotating each in a clockwise direction about a center of the second and third anchor. In another variant of the above method, the moving of the joint through the range of motion includes rotating and/or translating the first, second and third bones about and/or relative to one another.

In yet another embodiment, a method of joint stabilization comprises tensioning a first suture connected to a first bone location and a second bone location and also tensioning a second suture connected to the first bone location and a third bone location. In addition, alternatively or simultaneously while tensioning at least one of the first and second sutures, moving the joint through a range of motion. These steps allow determination of a range of motion available with incremental levels of tension. Tensioning ceases when a tension in the first and second sutures produces a limited range of motion in the joint.

In a variant of the above method, tensioning of the first suture is performed independent of the tensioning of the second suture. In an alternative to the above variant, an additional step involves implanting a first, second and third anchor at the first, second and third bone locations, respectively. In so doing, at least one anchor is implanted into a location corresponding to a native origin of one or more ligaments. In yet another alternative to this variant, the implanting of the first, second and third anchors further comprises placing at least one of the first, second and third anchors under the one or more ligaments. In another alternative of this variant, movement of the joint induces tension in the at least one ligament of the joint up to the tension creating the limited range of motion. For any attempt to impart a range of motion greater than the limited range of motion, movement of the joint is restrained from such attempted range of motion by the first and second sutures. In another alternative to this variant, an additional step of adjusting the tension in the first and second sutures occurs post-operatively to provide a greater range of motion in the joint.

In another aspect, the present invention relates to a system for soft tissue repair. In one embodiment, the system is for soft tissue repair in a joint and includes at least one suture anchor and at least one suture adapted to be loaded onto the at least one suture anchor. In a variant, the system can further include at least one tool for insertion of the at least one anchor and/or to adjust the tension in the at least one suture. In yet another variant, the system can include two or more tools wherein one tool is adapted for implantation of the at least one anchor and a second tool is adapted to adjust the tension in the at least one suture.

In yet another aspect, the present invention relates to a kit used to store items for a soft tissue repair. In one embodiment, the kit includes at least one suture anchor and at least one suture. In a variant, the kit further includes packaging adapted to store at least one of the suture anchor or the suture.

DETAILED DESCRIPTION

Figure 1:
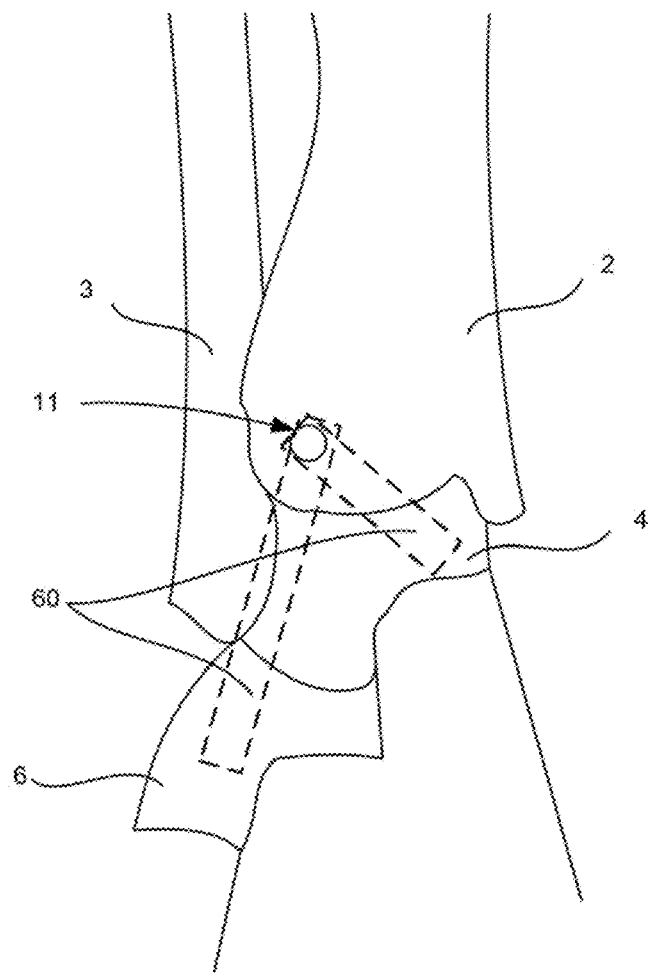
FIG. 1 illustrates an ankle joint with a first bone hole drilled into the tibia.

One aspect of the invention relates to a system and method for placing an adjustable joint stabilization construct in a joint of a patient. One particular example described herein is an adjustable suture brace, including at least one length of suture and at least one suture anchor. However, other materials than suture may be used if desired, and other structures or ways to secure suture (or other material) to desired bone locations may also be used instead of suture anchors. However, for ease of illustration, the various embodiments described herein will utilize suture and suture anchors.

In one embodiment, the system includes at least one suture and at least one suture anchor. The system preferably includes at least two suture anchors. The system can also include two or more lengths of suture. The system can also include at least one tool for inserting the at least one anchor and/or for adjusting the tension on a length of suture, as discussed below. Preferably, the system includes a dedicated tool for each individual suture anchor.

Such systems can be used in various methods for repair of a joint, in particular, for repair of soft tissue associated with a joint. In the various embodiments discussed below, the methods will be illustrated for use in the repair of an ankle joint, though such methods can be used in other joints, and for the repair of various soft tissues associated with such joints, elsewhere in the body of a patient.

As used herein, "soft tissue" may be, for example, meniscus, cartilage, capsule, ligaments and tendons, replacement grafts of any of these soft tissues, or the like. As used herein, the term "suture" means surgical suture as well as other filamentary or thread-like material, such as those constructed of synthetic material (e.g., PLGA, UHMWPE (ultra high molecular weight polyethylene), polyester, PEEK, Nylon, polypropylene, aramids (for example, Kevlar®-based fibers) or the like, or blends thereof), organic material (silk, animal tendon, or the like or blends thereof), or blends of both one or more organic materials and one or more synthetic materials. Alternatively, the term suture can also include thin metal wires. Resorbable sutures can also be considered where the operator would prefer that the suture eventually degrades over time, presumably after the surgical repair has healed. Where filamentary structures are used, they may include elastic properties, though such elasticity should be limited. While any of these materials may be used, it is preferable, and is disclosed herein, that the various sutures of the present invention be constructed out of suture, such as UHMWPE, polyester or blends thereof.

Another aspect of the present disclosure relates to a kit including one or more items, such as a suture anchor. In one embodiment, the kit includes at least one suture anchor, at least one suture, an insertion tool, at least one drill and at least one drill guide. The kit preferably includes at least two suture anchors. In other embodiments, the kit can include at least one suture anchor, at least one suture and an insertion tool. In other embodiments, the kit can include at least one suture anchor and at least one suture. In any one of the above embodiments, the kit or individual items and combinations thereof may be disposed within a packaging or a plurality of packages. For example, all of the items of the kit may be disposed within a single packaging. In another example, all of the instruments may be in one packaging, all of the implants in another, and all of the sutures in yet another. Of these three groupings, any two types may be in a single packaging while the third is in another. The items included in the kit may also be individually packaged. For example, each anchor may be in its own packaging. Packaging each item in the kit separately or in different combinations may improve the sterility of the items in preparation for and during surgery. One reason for this is that some items may be required prior to others when implanting the system. For example, the insertion tool could remain in its own packaging while the suture anchor is implanted into bone. Other advantages may be realized with various combinations of packaging depending on the nature of the surgical operating area and the type of surgery performed, among other reasons.

Another aspect of the present invention relates to a method of placing an adjustable joint stabilization construct in a joint of a patient. One embodiment of the method generally involves augmenting a primary repair of a joint. As used herein, "primary repair" means a standard orthopedic repair, such as a soft tissue repair, joint replacement, or the like. In particular, as discussed throughout the illustrated embodiments and examples herein, the primary repair will be the repair, replacement or reattachment of soft tissue, in particular, ligaments and tendons and replacement grafts of same, to bone. As used herein, "augmentation" and its iterations means a secondary repair intended to protect, support, and/or limit movement of the primary repair.

Figure 2:
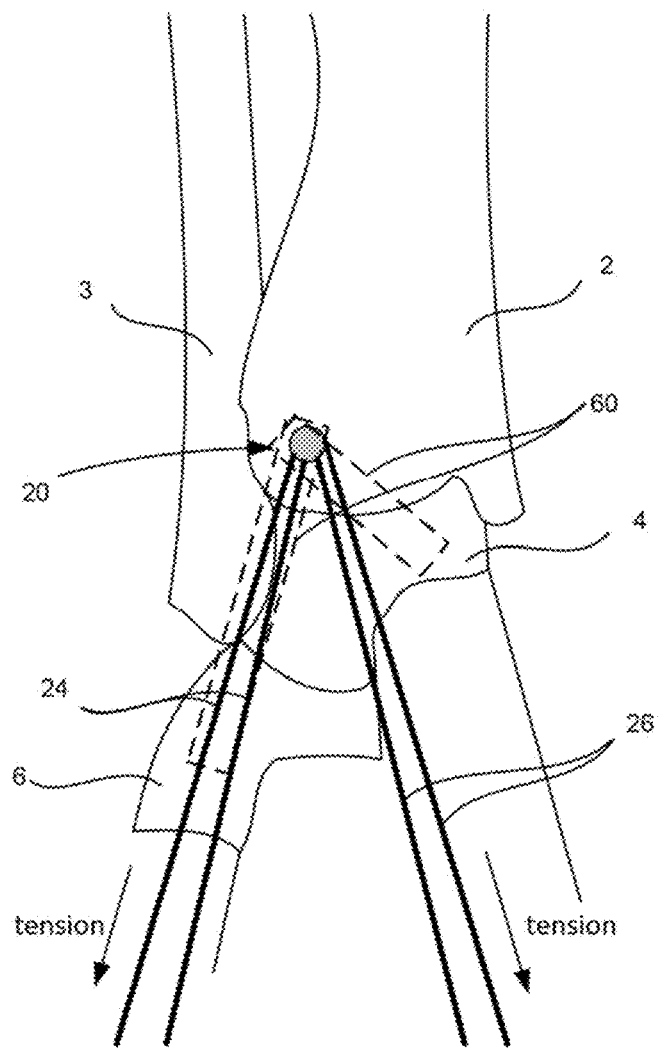
FIG. 2 illustrates an anchoring step in one embodiment where a first anchor loaded with two sutures is implanted into a bone at a first bone hole.
Figure 3:
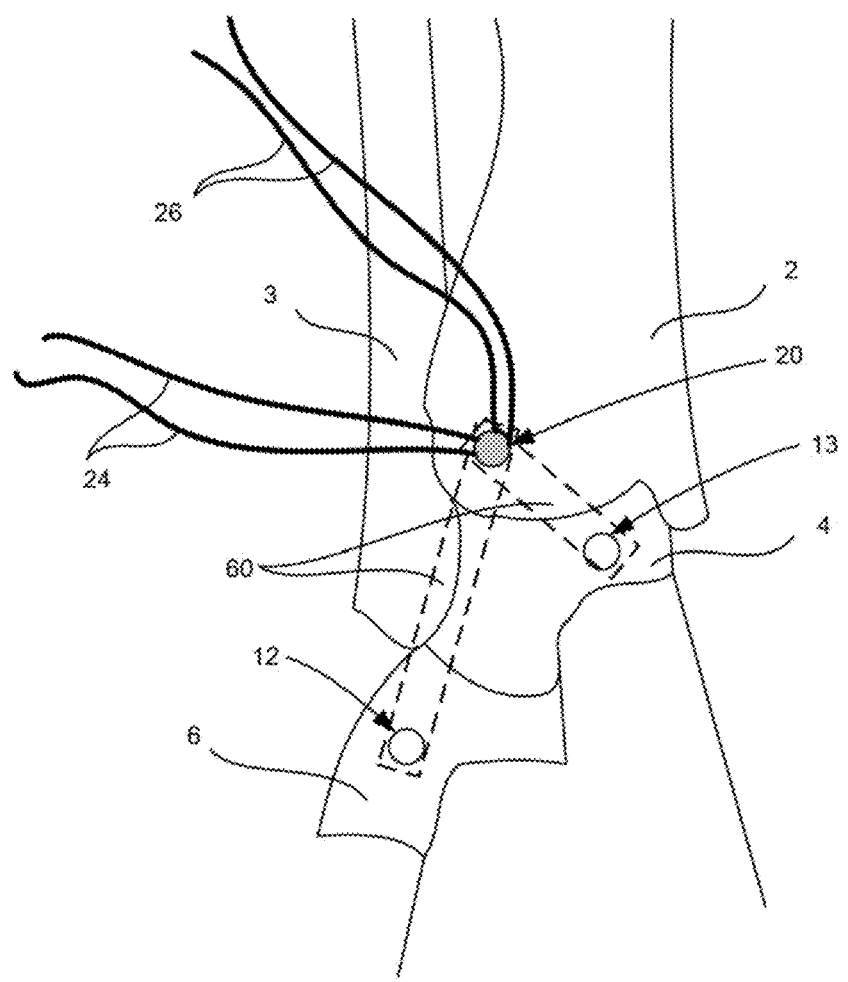
FIG. 3 illustrates a location of second and third bone holes for the placement of second and third anchors, respectively.

For the various embodiments herein, the primary repair can be performed by standard means or by any means as known to those of ordinary skill in the art. For example, as in the example of securing soft tissue to bone, standard procedures involving suture, suture anchors, drills and drill guides, and the like may be used. Further, primary repair of the joint can be done before, simultaneously with, or after the augmentation procedure. The technique of this embodiment, which will serve as an exemplary illustration of the general procedure disclosed herein, applies to a deltoid repair in an ankle joint and is illustrated in FIGS. 1 through 6. The augmentation procedure begins by identifying a placement location for suture anchors at the repair site. At least one of the placement locations for the anchors may correspond to a native attachment site of the soft tissue, in this example, of the deltoid ligament 60, as shown in FIGS. 1 and 3, for example. As such, each anchor that is positioned at such a native site will, at the conclusion of the repair, be positioned underneath or adjacent to the soft tissue being reattached thereto. In certain embodiments, where each anchor is placed at a native attachment location, the anchor can be positioned prior to securing the soft tissue, or alternatively, the anchor can be passed through the ligament end and into the bone. Where the anchors of the suture structure are placed through the ligament, such anchors can also be used to secure the ligament to the bone, thus removing the need to include a separate securement for the ligament repair. The above ligament placement possibilities are considered in the illustrations of FIGS. 1-6, which show ligaments 60 with a hatched outline to denote that the ligaments may be placed prior to, simultaneously, or following the implantation of the suture structure.

However, placement at the native origin of a ligament is not mandatory for any of the suture anchors and variants can utilize other bone locations for the placement of anchors. For example, since one of the primary goals is to position an implant construct (such as suture anchors and sutures) to limit over-exertion of a joint, or an anatomical structure associated with the joint, in at least one direction, the best positioning of the suture anchors may be at a location other than a native soft tissue attachment site. To this end, in certain embodiments, none of the suture anchors are positionable at such a native site, and instead, the anchors are positioned elsewhere in bone relative to the joint. In other embodiments, some, but not all of the anchors may be at a location other than a native soft tissue attachment site. For ease of reference, FIGS. 1-6 illustrate an embodiment where the suture anchors are positioned at native soft tissue attachment sites.

The act of positioning a suture anchor in bone can be performed in any manner as generally known in the art. Typically, a bone hole is formed into which the suture anchor is positioned. Alternatively, self-tapping suture anchors are also known and can be used, whereby no bone hole needs to be formed, or a smaller pilot hole can be used. Continuing with the example of a non-self-tapping anchor in the embodiment illustrated in FIGS. 1-6, a drill and drill guide as known to those of skill in the art are used to drill bone holes for the placement of anchors used as part of an adjustable suture structure. In FIGS. 1-6, the structure is a brace, but other structures are contemplated, as described above. The first hole 11 is prepared at a native origin for an end of a ligament 60 connected to a medial malleolus of the tibia 2, as best shown in FIG. 1. Once the first hole 11 is prepared, the drill is removed from the drill guide, and the drill guide may remain firmly in place at the first hole 11. To prepare the first anchor 20 for placement into the bone, the anchor 20 is positioned on an insertion tool. At least one suture, and as illustrated, two sutures 24, 26, are loaded onto the anchor 20 such that four suture ends, also known as tails, two from each suture, extend from the anchor 20 (FIG. 2). The insertion tool is then placed through the drill guide (if still positioned at the bone) and implanted into the first hole 11. In one example, implantation can be performed by tapping the insertion tool with a mallet. Any additional steps to secure the anchor are performed at this time including any step that is specific to the anchor used.

Figure 4:
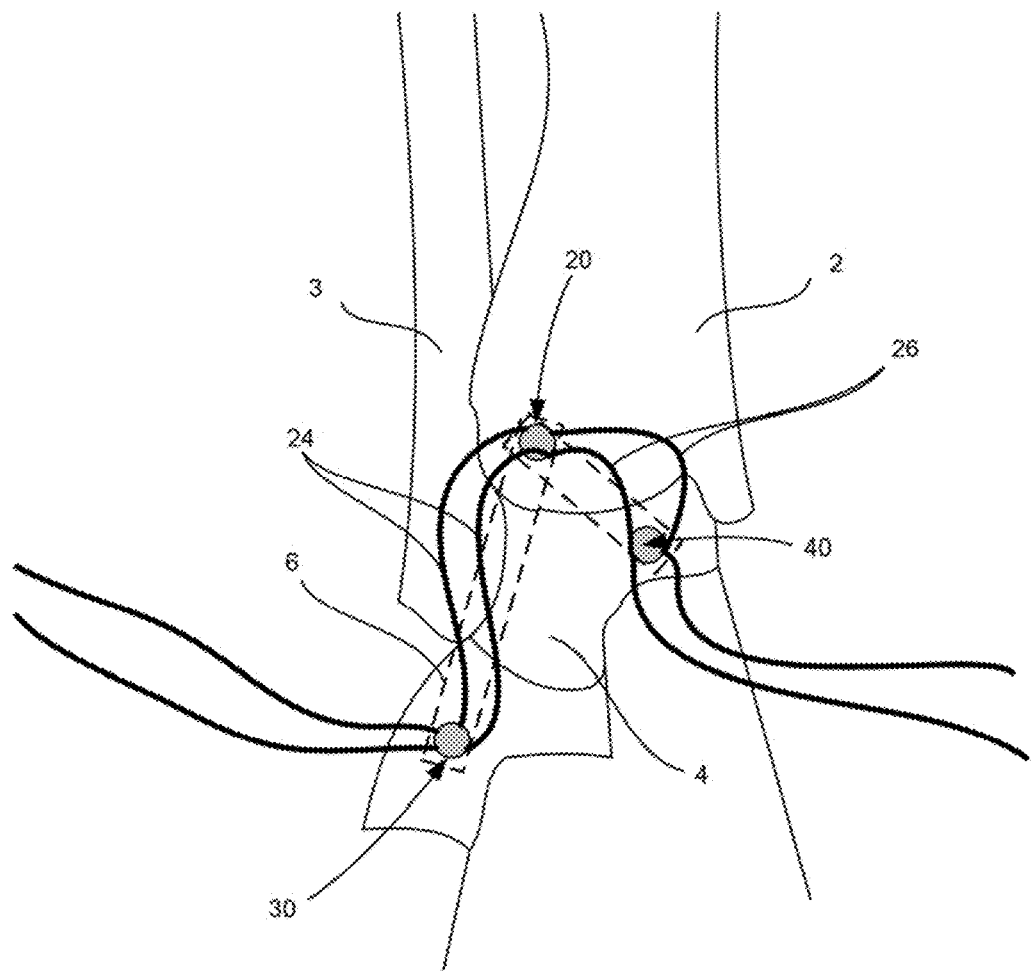
FIG. 4 illustrates the implantation of second and third anchors at the second and third holes so that each of the two sutures as illustrated in FIG. 1 are secured between one of the first and second anchors and the first and third anchors.

With the first anchor 20 secured in the first hole 11 (FIG. 2), or prior to insertion of the first anchor, at least one of the free ends of the first suture 24 are loaded into a second anchor 30 and at least one of the other free ends of the first or second suture 24, 26 are loaded into a third anchor 40. As shown in FIG. 4, both free ends of first suture 24 are loaded into second anchor 30 while the free ends of second suture 26 are loaded into third anchor 40. The second and third anchors are any anchor type that can be loaded with a suture and implanted into a bone (in any order) to maintain fixation with the bone while the suture is tensioned. Put another way, the second and third anchors, just as the first anchor, must be able to withstand pull out forces when operational tension is applied to the sutures. Prior to the implant of the second and third anchors 30, 40 into designated bone locations at the joint, second and third anchor locations are identified in a similar manner to that of the first anchor location described above and second and third holes are drilled. Additionally, the second and third bone holes, while they can simply be positioned at native soft tissue attachment locations, as discussed with first anchor 20 above, an operator (such as a surgeon) can instead examine the biomechanics of the particular joint and determine locations other than the native soft tissue attachment locations for a second (and third, fourth, etc. as desired) suture anchor that can sufficiently augment the soft tissue repair. As shown in FIG. 3, for example, the second anchor hole location 12 is at the sustentaculum tali 6 and the third anchor location 13 is at the deep deltoid insertion of the talus 4. The second and third anchors 30, 40 are then implanted into the second and third anchor holes 12, 13, respectively, and the suture can be loaded into the anchor prior to or after insertion into the bone holes. The method of implantation is a function of the anchor type used. For example, the anchors used can be self-tapping suture anchors. When self-tapping suture anchors are used, no drilling to prepare a hole in the bone is required. Instead, the anchor creates a hole as it is driven into the bone. The anchors are secured so that both the first suture 24 and the second suture 26 include slack between anchor points, as best shown in FIG. 4.

The suture anchors used in the various embodiments of the present invention can be any known in the art that can perform the procedural steps herein. For example, of the anchors described above that are used to assemble the adjustable suture structure, suitable suture anchors can be the Iconix™ and ReelX SST® anchors. In this example, the first anchor 20 can be an Iconix™ fixation device by Stryker. To prepare for the implant of the Iconix, an Iconix drill guide and a 2.3 mm drill are used to drill first hole 11. The drill is then removed and the drill guide is left in place on the bone surface. The insertion tool (not shown) is then loaded with the Iconix. The Iconix includes a sleeve element (not shown) with first and second sutures 24, 26 running therethrough. From its position on the insertion tool, the Iconix is passed through the Iconix drill guide to the first hole 11 located in the tibia 2. To implant the Iconix into the hole 11, the insertion tool presses the sleeve into the hole and in so doing the sleeve element folds within the hole so that contact is made with walls inside the hole. The contact creates a frictional engagement between walls in the hole and the sleeve and the insertion tool is untethered and otherwise removed. The structure of the first anchor with the insertion tool removed should be as it appears on FIG. 2, with suture ends extending outwardly from the hole 11 and the sleeve secured within hole 11 and therefore not visible. Because there are two sutures in this example, there are a total of four free ends of suture extending from the implanted first anchor 20. To increase engagement between the anchor 20 and the hole 11, the ends of the first and second sutures 24, 26 are grasped and pulled, as shown in FIG. 2. The resultant tension in the sutures causes the sleeve inside the hole to activate and otherwise sets itself to create additional engagement with the walls of the hole 11. The installation of the Iconix anchor is described more fully in U.S. application Ser. No. 13/303,849, published as U.S. Pat. Pub. 2013/0131722, the entirety of which is hereby incorporated by reference herein.

The second and third anchors 30, 40 of this example can both be 4.5 mm ReelX SST® anchors by Stryker ("ReelX anchors"). To drill bone holes for placement of the ReelX anchors, a 3.25 mm BioZip drill is used. The ReelX anchors are then prepared by securing each one on a compatible inserter (not shown) having a handle and shaft. To load sutures into a first ReelX anchor 30, the ends of first suture 24 extending from the first anchor 20 at the first bone hole are loaded through an aperture or apertures in the first ReelX anchor 30. Once the first suture 24 is placed through the ReelX 30, the suture 24 should be checked to ensure it has a small amount of tension and that each end of the suture has an equal amount of slack prior to implanting the ReelX 30 into the bone at the second bone location 12 at the sustentaculum tali 6. Of course, in a variant, the second location can also be the deep deltoid insertion of the talus 4. A mallet is used to secure the ReelX 30 into place in the bone hole. The ReelX will be in position when its surface is flush with a cortical surface of the bone. At this juncture, the suture 24 is secured at two locations, one by the Iconix anchor 20 and the other by the ReelX anchor 30. The same steps are followed to secure the second ReelX 40 loaded with second suture 26 to the third bone hole 13. To tension the first or second suture 24, 26, the handle of the inserter is turned clockwise. For the ReelX in particular, up to three complete revolutions can be made. A locking point is included for every 60 degrees of revolution and approximately 1.5 mm of suture is advanced for every 60 degrees of rotation. The above process with a ReelX anchor is repeated for second suture 26 at the third bone location 13 on the deep deltoid insertion of the talus 4. The structure of the ReelX anchor, and its method of use, is described more fully in U.S. patent application Ser. No. 12/206,643, published as U.S. Patent Publication 2010/0063542, the entirety of which is hereby incorporated by reference herein.

Figure 5:
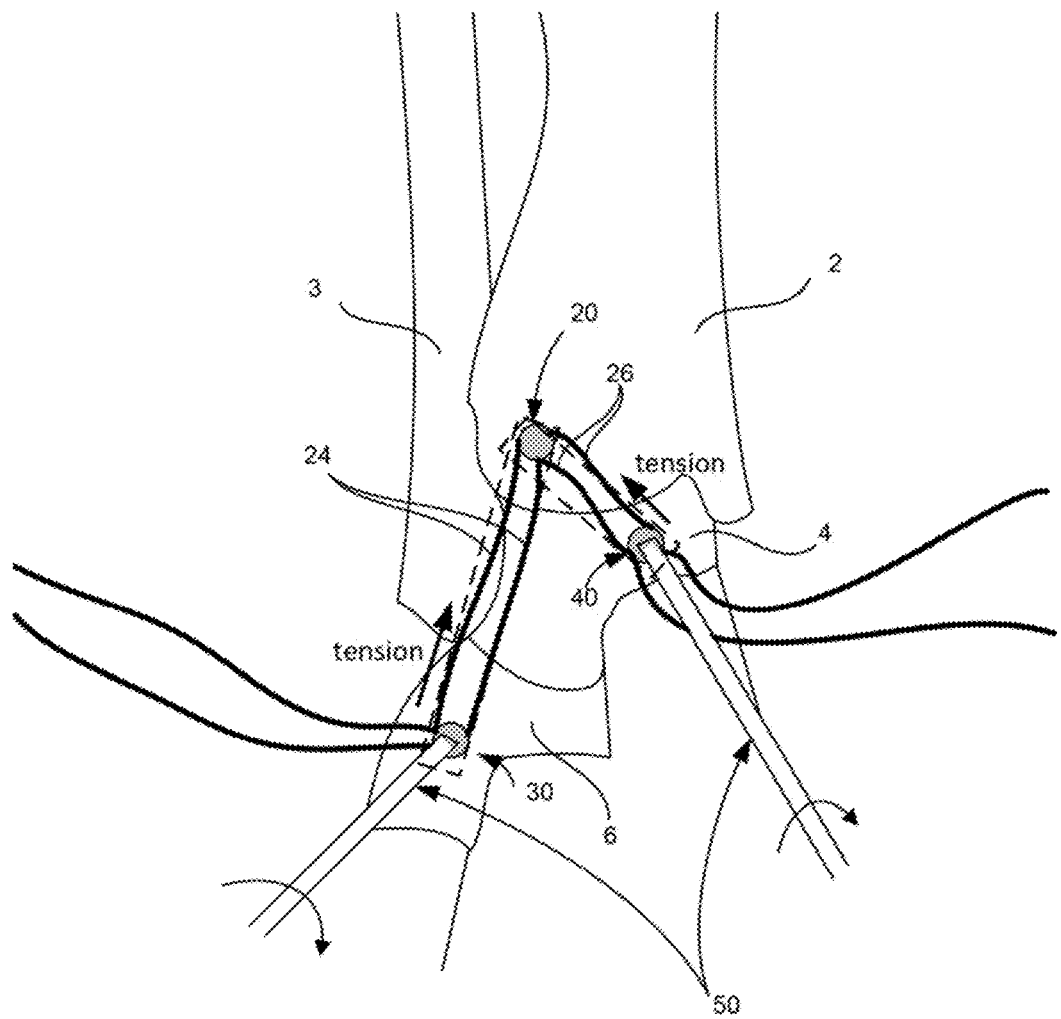
FIG. 5 illustrates a tensioning step where the sutures secured to the anchors are tensioned. Although both the first and second sutures are shown as being tensioned simultaneously in the illustration, some embodiments include a tensioning step where only one of the first and second sutures is tensioned at any given time.

With the first, second and third anchors 20, 30, 40 all secured to bone and the first and second sutures 24, 26 in place and engaged with the anchors, the sutures are ready to be tensioned. The adjustable suture structure as it appears prior to tensioning is shown in FIG. 4. Tensioning begins with one suture and then the other, such as first with first suture 24, which, as in FIG. 5, is tensioned through tightening of the second anchor using an actuating tool 50 with a tip secured to the second anchor. In one example, the actuating tool 50 is compatible with ReelX anchors and is used to actuate ReelX anchors, such as by clockwise rotation of the anchor about a center of the anchor, to increase tension in the suture, as best shown in FIG. 5. This is also known as "dialing in" the tension. Tensioning is performed incrementally in this procedure. Accordingly, the initial tensioning of the first suture 24 is only a fraction of a final tension in the suture and thus tensioning ceases during this step prior to reaching the final tension. For clarity, this initial tension in the first suture will be referred to as a first increment of tension in the first suture. The final tension in the suture will correspond with a range of motion in the joint deemed satisfactory for future physical activity undertaken by the patient (hereinafter "post-operative range of motion").

The post-operative range of motion that will be established through tensioning is patient specific, joint specific, anchor location specific, etc., and can depend on many factors, such as the physiological characteristics of the patient and the type and extent of injury in the joint. Where, as here, the adjustable suture structure is used to augment a standard repair, the post-operative range of motion will be limited sufficiently to ensure that tension in the repaired ligaments never reaches an amount that would damage or destroy the repair. Put another way, over-exertion of the joint is prevented. This improves the success rate of the repair. Over-exertion can be prevented in one, two or three axes of motion. An example to illustrate how the post-operative range of motion protects the joint is as follows. If it is determined that in order to prevent damage to the repaired ligaments during recovery, the ligaments cannot sustain tensile forces greater than 10 N, then the sutures can be tensioned to restrain movement in one or more axes of the joint so that the tension in the ligaments is never greater than 10 N. By preparing the adjustable suture structure in this way, the ligaments are protected from over-exertion during a surgical recovery period. Put another way, the suture construct operates as a "safety net" to allow limited mobility of the joint but prevent over-exertion of the ligaments, such as would occur in an excessive movement of a joint in one or more directions.

With the first suture 24 having a tension in the amount of the first increment of tension, the ankle joint is then moved and/or manipulated through a range of motion to determine the extent to which motion is possible at the first incremental tension (not shown). This allows the range of motion to be compared against that available prior to tensioning, or, in later increments of the procedure, the difference in the range of motion between increments. "Range of motion" as referred to herein means rotation and/or translation of the elements in the joint to determine the extent to which the joint can be positioned in one, two or three dimensions. Rotation can be about a center of the joint or it can be relative rotation between bones. Translation can be relative to a center of the joint or it can be one bone relative to another. As an example, the ankle joint can be manipulated to determine the maximum angle of flexion or extension. It can also be rolled to determine the maximum angle of pronation, supination, eversion and inversion. When the range of motion with the first suture 24 subject to a first increment of tension is compared to the adjustable suture structure prior to any tensioning, a reduced range of motion should be realized. The range of motion is also compared with the sought after post-operative range of motion. At this step in the procedure, because the tensioning process is iterative, the tension in first suture 24 should be less than the tension corresponding to the post-operative range of motion. Also, by only partially tensioning the first suture as a first tensioning step, the remaining slack in the first suture allows some flexibility in tensioning the second suture 26, making adjustments to the second suture easier to perform.

Figure 6:
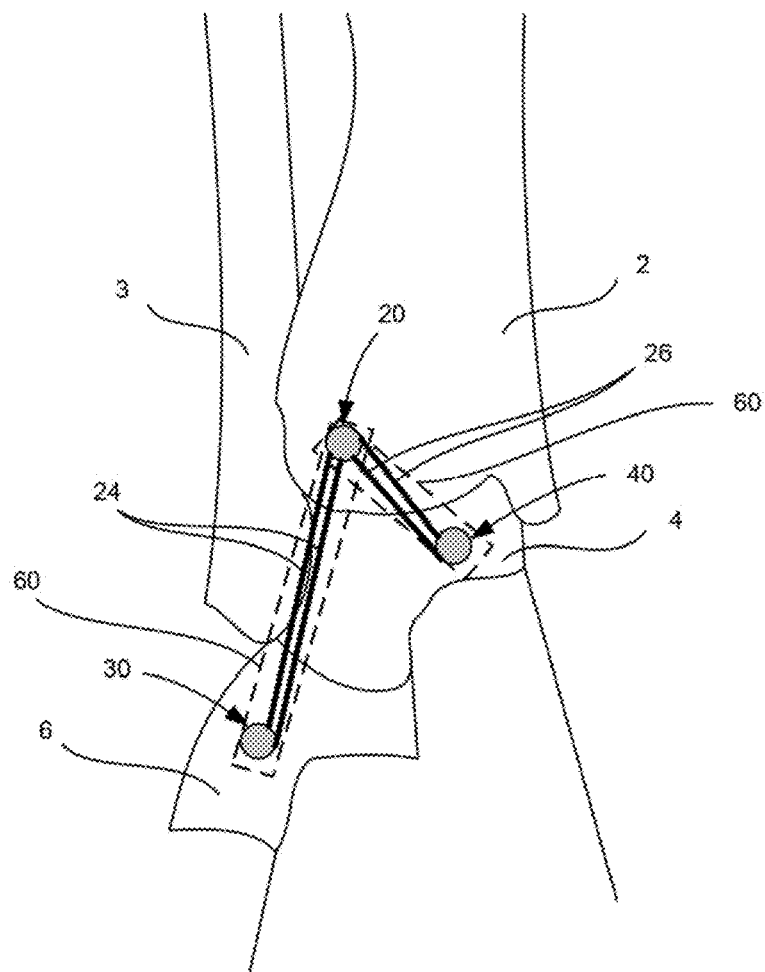
FIG. 6 illustrates the sutures after tensioning is completed and sufficient to limit movement of the joint to a post-operative range of motion that provides stability to the joint.

After tensioning the first suture 24, the same approach is applied to tension the second suture 26 (and further sutures, if present). The tool used to adjust the tension in second suture 26 can be the same actuating tool 50 as used to tension first suture 24 or it can be another tool. The tensioning process is shown in FIG. 5. Second suture 26 is tensioned until a first increment of tension in the second suture 26 is obtained. The amount of tension in the second suture 26 is independent relative to the tension in the first suture 24, but may be similar, or even substantially equal in some cases. When the tension in second suture 26 reaches the first increment, the joint is manipulated to test the range of motion. The range of motion at this juncture is further reduced relative to the range of motion after tensioning first suture 24 as described above because both first and second suture 24, 26 are now tensioned to first increments. The above process is then repeated from the beginning. Thus, the tensioning process can be described as tensioning first suture 24, checking the range of motion in the joint, tensioning second suture 26, checking the range of motion in the joint, tensioning first suture 24 a second time, checking the range of motion in the joint, and so on. As this iterative process continues, the tension in each suture 24, 26 progressively increases, reducing the range of motion and bringing it closer to the post-operative range of motion. Either prior to tensioning, during or after, the stray free ends of the sutures extending beyond the second and third anchors 30, 40 are cut and otherwise removed. Once the free ends are removed and the tensioning process is complete, the adjustable suture structure appears as shown in FIG. 6. In a variant, the exact order of each iteration in the tensioning process can vary. For example, after the first tensioning of first suture 24 and the first tensioning of second suture 26, second suture 26 can be tensioned again after checking the range of motion of the joint, despite having only tensioned first suture 24 once. This provides flexibility in the tensioning procedure and allows surgeons to adapt to changing surgical conditions and any unique physiological characteristics of the patient. Further, though a single insertion tool can be used, having dedicated tools for each of the second and third anchors provides for simplified suture adjustment throughout the procedure.

Once the tension in the sutures controls the range of motion so that it is limited to the intended post-operative range of motion in the joint, the ligaments will heal without excess strain. In the event that tensile stresses in the axes of the ligaments exceeds an amount that would cause damage to the ligaments, the tension set in the sutures will limit movement in the relevant axes to prevent such tension from being borne by the ligaments, as described above, and thus prevent damage to the ligaments or other related injury. Put another way, any attempt to impart a range of motion greater than the described limited range of motion will be restrained by the tension in the first and second sutures 24, 26.

The stabilization of the joint can also involve staged recovery. For example, if a recovery time for the healing of repaired ligaments is of a long duration, but the initial range of motion set through the placement of the adjustable suture structure is severely limited to allow for healing, the tension in the sutures may be surgically reduced in follow up surgery during the recovery period as the ligaments heal to assist in the recovery. This would be based on the increased load bearing capacity of the ligaments relative to that available immediately following surgery. In this way, the range of motion in the joint can be increased at least to some extent prior to the lapse of the full time period for recovery. Alternatively, suture anchors that can ease suture tension automatically, either within a set timeframe or by remote control, or the like, can also be used to increase the range of motion in the joint as recovery progresses.

In another embodiment, the first suture is initially tensioned simultaneously with movement of the ankle joint through a range of motion. In one variant, simultaneous movement of the joint may occur periodically. In others, it may occur with regularity or constantly. Thus, the range of motion in the joint is observed during the tensioning process. In a manner similar to the above embodiment, the tension in the first suture is increased to a first incremental tension. As above, examples of anchors used for the adjustable suture structure in this embodiment include the Iconix and the ReelX. When the first increment of tension is reached in the first suture, then the same process of simultaneously tensioning and moving the ankle joint through a range of motion is applied to the second suture. In adjusting the suture structure this way, the range of motion in the joint is observed at all times during the tensioning process. Because the method is iterative, tensioning of the first suture is repeated after tensioning of the second suture and this continues until movement of the joint is limited to the post-operative range of motion is achieved. Of course, in a variant, the tensioning sequence can be in another order. For example, second suture, first suture, second suture, first suture and so on. In another example, the order can be first suture, second suture, second suture, first suture, or any other combination deemed suitable under the applicable surgical conditions.

In another embodiment, the first and second sutures are tensioned simultaneously until a first incremental tension is reached. From this point, the joint is moved through a range of motion as described in the above embodiments. Based on the range of motion at the first increment of tension, the sutures are once again tensioned simultaneously and the process is repeated until movement of the joint is limited to the post-operative range of motion.

In yet another embodiment, both the first and second sutures are tensioned simultaneously and the joint is placed through a range of motion during the tensioning process. Here, because both sutures are tensioned at the same time and the resultant range of motion is observed during the tensioning process, the sutures are tensioned in a single step ending when the range of motion in the joint equals the post-operative range of motion.

In still further embodiments, combinations of the above method steps may be performed. For example, initially, the first suture can be tensioned simultaneously with moving the joint through a range of motion. Then, both the first and second sutures can be tensioned simultaneously while moving the joint through a range of motion. This can be followed by tensioning the second suture. It is contemplated that any combination of steps using the above described techniques, alone or in combination, can be used to tension the sutures.

In any one of the above embodiments, the first, second or third anchor can be implanted into the first, second or third bone hole, respectively, before being loaded with the at least one suture. The adjustable suture structure as contemplated herein is not limited to require that sutures be loaded onto anchors prior to implantation, nor must a particular combination of anchors loaded with sutures prior to and after implantation be provided. For example, the first anchor can be implanted into the first bone hole and then loaded with the at least one suture, while the second anchor can initially be loaded with a suture followed by implantation into the second bone hole. For the same adjustable suture structure, the third anchor can then be implanted into the third bone hole and then loaded with a suture. In other examples, sutures can be loaded onto anchors before or after they are implanted, and the order of suture loading or implantation is not limited by the manner utilized for other anchors forming the adjustable suture structure.

In any one of the above embodiments, the first and second sutures can be used as a standalone construct to replace ligaments, such as the deltoid, in the ankle joint. Here, the procedure for installing and otherwise preparing the adjustable suture structure is the same as described above, except there is no step of performing a standard ligament repair. Because there are no performance characteristics for newly recovering ligaments to refer to in determining the tension needed for the sutures, other factors are considered. For example, an assessment of the patient's physiology is made to determine an acceptable post-operative range of motion in the joint with the adjustable suture structure in place, and the sutures are tensioned accordingly, using techniques as described in any of the above embodiments. In this case, the post-operative range of motion may be less than that existing in a healthy joint to avoid potential deleterious effects to tissue surrounding the suture structure or other complications in view of the surgery as performed.

Still further, in another embodiment, the suture construct can be implanted relative to a joint and soft tissue that may not require repair as discussed above, but instead may present weakness or instability. In this instance, the suture construct can again guard the weakened joint from over-exertion, which might cause significant injury, but is not implanted as a corollary to soft tissue repair. Further, the anchors in this embodiment may not be positioned at the native soft tissue attachment sites, but instead would be positioned around the soft tissue such that the "safety net" benefit is achieved but the soft tissue is otherwise not disturbed.

In any one of the above embodiments, the method described can be employed in other ligaments in the ankle joint. For example, the method can be employed in the anterior talofibular ligament, the calcaneofibular ligament and spring ligament. In still further embodiments, the method can be employed in joints other than the ankle. For example, the medial collateral ligament in the knee and the elbow, among others.

In any one of the above embodiments, a repair can involve a single suture anchored at two locations that forms a suture structure. Similarly, three, four or more sutures can be used where it would be deemed beneficial. An example of a single suture repair is a lateral ankle repair to augment the anterior talofibular ligament. In this example, the procedure begins with a standard Brostrom repair of the ligament. Alternatively, the augmentation can be performed prior to the Brostrom repair. With a Brostrom incision created and the surgical site prepared, a first bone hole is drilled for the implant of an anchor, for example, an Iconix anchor, in the same manner as described for the deltoid repair, but in this case, the anchor is implanted into the distal fibula. With the first hole drilled, the Iconix is implanted. In the event that the Iconix anchor is loaded with two sutures, one of the two is cut and discarded at this time. As described above, a second bone hole is prepared using a drill, such as a 3.25 mm BioZip drill. The second bone hole is drilled into the non-articulating portion of the talus. This hole accommodates the implant of another suture anchor, such as the 4.5 mm ReelX anchor. The first and second bone holes are located in accord with native origins of the ligaments for the superior anterior talofibular ligament. The free ends of the suture extending from the Iconix anchor are then loaded through the 4.5 mm ReelX anchor. As above, the ReelX is then implanted into the second bone location so that the suture includes at least some slack. With both anchors secured and thus holding the suture in place, various combinations of the above described techniques can be used to increase the tension in the suture and test the range of motion in the joint. Once the tension in the suture limits movement of the joint to the post-operative range of motion, the adjustable suture structure is ready for use by the patient. At this time, the remaining suture ends are cut so that no excess suture ends extend from the ReelX.

In the various embodiments of this method, there are no particular limitations on the number of bones connected by the sutures. The number of bones used to secure the anchors of the adjustable suture structure is generally a function of the type of augment or standalone construct used. For example, the deltoid repair involves three bones and the anterior talofibular ligament repair involves two bones.

Whether it is used to augment a primary standard repair or as a standalone construct, the system described herein including an adjustable joint stabilization construct can increase stability when compared to standard repairs. Use of the system also provides a patient with immediate use of the joint following surgery, even though in some cases such use is limited, such as in many instances where the system is used to augment a traditional standard repair. This is in contrast with standard repairs where in many cases a patient must be placed in a cast following surgery so as to avoid rupturing or otherwise damaging the repaired ligament(s). Put another way, the embodiments described herein minimize joint immobilization, alleviate restricted patient mobility, could potentially reduce the need for or all but eliminate external bracing for certain procedures and/or for certain lengths of time following surgery, and substantially reduce recovery times following surgery.

Advantages of the system when used as an augment to a primary standard repair include that it provides additional support for the ankle and ligament structures during the healing process of the ligament(s). The system also provides an internal "safety net" because it decreases the chance of failure of the ligaments, particularly in the time period immediately following surgery. This is because the tension in the sutures prevents excess stress from being placed on the primary ligament repair.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of joint stabilization using a suture configuration to stabilize a joint comprising:
   implanting a first anchor into a first location in a first bone, a first suture loaded into the first anchor, the first suture having first and second ends;
   loading at least one of the first and second ends of the first suture into a second anchor;
   implanting the second anchor into a second location in a second bone such that there is slack in a portion of the first suture between the first anchor and the second anchor; and
   tensioning the first suture and moving the joint through a range of motion, the moving of the joint either alternating with the tensioning or occurring simultaneously with the tensioning, until the tensioning increases tension in the first suture to a final tension at which the range of motion of the joint is limited to prevent over-exertion of the joint in at least one direction of motion,
   wherein the joint is moved through a working range of motion at least once when tension in the first suture is less than the final tension, the working range of motion providing an improved indication of an amount of additional tension needed to reach the final tension than that available prior to the movement of the joint through the working range of motion.

2. The method as recited in claim 1, wherein prior to implanting the first and second anchors, the first and second locations are established based on native origins of one or more ligaments.

3. The method as recited in claim 2, wherein implanting the first and second anchors further comprises placing each anchor under a repaired ligament such that the final tension in the first suture augments and protects the repaired ligament to stabilize the joint.

4. The method as recited in claim 3, wherein the joint is exerted in at least one direction of motion such that the exertion is up to and including an amount that causes tension in the first suture to reach the final tension, the final tension in the first suture preventing over-exertion of the joint in the at least one direction of motion by preventing any additional movement of the joint in the at least one direction of motion.

5. The method as recited in claim 1, further comprising a second suture, wherein the loading step further comprises loading the second suture into the first anchor so that third and fourth ends of the second suture extend from the first anchor.

6. The method as recited in claim 5, wherein the method further comprises:
   loading the second suture into a third anchor after implanting the first anchor;
   prior to tensioning the first suture or the second suture, implanting the third anchor into a third bone location in the second bone or a third bone such that the second suture between the first anchor and third anchor includes slack; and
   after tensioning the first suture to an intermediate tension lower than the final tension, tensioning the second suture and moving the joint through the range of motion, the moving of the joint either alternating with the tensioning of the second suture or occurring simultaneously with the tensioning of the second suture.

7. The method as recited in claim 6, wherein after tensioning the first suture to the intermediate tension, the sequence of tensioning the first suture between the first and second anchors followed by the second suture between the first and third anchors is repeated one or more times until the tension between both the first and second anchors and first and third anchors corresponds to the limited range of motion.

8. The method as recited in claim 7, wherein implanting the first, second and third anchors comprises placing each anchor under one or more repaired ligaments and then into bone at the first, second and third bone locations, respectively, such that the final tension in the sutures augments and protects the repaired ligament or ligaments to stabilize the joint, a final tension in the first suture being different than a final tension in the second suture.

9. The method as recited in claim 1, wherein implanting the first and/or second anchor into the first bone is completed prior to loading the first suture into the first and/or second anchor.

10. A method of joint stabilization using one or more sutures to stabilize a joint comprising:
tensioning a first suture connected to a first bone at a first location and a second bone at a second location, the first location corresponding to a first native origin of a first ligament and the second location corresponding to a second native origin of the first ligament;
moving the joint through a range of motion to determine a range of motion of the first bone relative to the second bone available with incremental levels of tension, the moving of the joint either alternating with the tensioning of the first suture or occurring simultaneously with the tensioning of the first suture;
ceasing the tensioning of the first suture and moving of the joint prior to reaching a first tension, the first tension limiting the range of motion sufficiently to prevent over-exertion of the joint in at least one direction of motion;
tensioning a second suture connected to the first bone or a third bone at a third location and the second bone or a fourth bone at a fourth location, the third location corresponding to the first native origin of a second ligament and the fourth location corresponding to a second native origin of the second ligament;
moving the joint through a range of motion to determine a range of motion available between the bones connected by the second suture with incremental levels of tension, the moving of the joint either alternating with the tensioning of the second suture or occurring simultaneously with the tensioning of the second suture;
ceasing the tensioning of the second suture and moving of the joint prior to reaching a second tension wherein the range of motion is sufficiently limited to prevent over-exertion of the joint in at least one direction of motion; and
repeating the tensioning and moving steps for the first and second sutures one or more times until the tension in the first and second sutures limits the range of motion in the joint in at least one direction of motion.

11. The method as recited in claim 10, further comprising implanting a first anchor into the first bone, a second anchor into the second bone and a third anchor into the third bone, the first suture extending between the first anchor and the second anchor, and the second suture extending between the first anchor and the third anchor.

12. The method as recited in claim 11, wherein tensioning of the first suture further comprises interconnecting a tool with the second anchor and manipulating the tool to cause rotation of the second anchor and wherein tensioning of the second suture further comprises interconnecting the tool with the third anchor and manipulating the tool to cause rotation of the third anchor.

13. The method as recited in claim 12, wherein the tool interconnected with the second anchor is different from the tool interconnected with the third anchor, wherein manipulating the tools involves rotating each in a clockwise direction about a center of the second and third anchor.

14. The method as recited in claim 10, wherein moving the joint through the range of motion includes rotating and/or translating the first, second and third bones about and/or relative to one another.

15. A method of joint stabilization comprising:
tensioning a first suture connected to a first bone location and a second bone location and tensioning a second suture connected to the first bone location and a third bone location;
moving the joint through a range of motion, the moving of the joint either alternating with the tensioning of the first or second suture or occurring simultaneously with the tensioning of the first or second suture, to determine a range of motion available with incremental levels of tension; and
ceasing the tensioning when a tension in the first and second sutures produces a limited range of motion in the joint.

16. The method as recited in claim 15, wherein tensioning of the first suture is performed independent of the tensioning of the second suture.

17. The method as recited in claim 16, further comprising implanting a first, second and third anchor at the first, second and third bone locations, respectively, such that at least one anchor is implanted into a location corresponding to a native origin of one or more ligaments.

18. The method as recited in claim 17, wherein implanting the first, second and third anchors further comprises placing at least one of the first, second and third anchors under the one or more ligaments.

19. The method as recited in claim 18, wherein movement of the joint induces tension in the at least one ligament of the joint up to the tension creating the limited range of motion, and for any attempt to impart a range of motion greater than the limited range of motion, movement of the joint is restrained from such attempted range of motion by the first and second sutures.

20. The method as recited in claim 19, further comprising adjusting the tension in the first and second sutures post-operatively to provide a greater range of motion in the joint.

* * * * *